United States Patent [19]

Brendel et al.

[11] Patent Number: 5,686,589
[45] Date of Patent: Nov. 11, 1997

[54] ESTERS AND AMIDES OF SUBSTITUTED PHENYL AND PYRIDYL AMINO CARBOXYLATES

[75] Inventors: Klaus Brendel, Tucson, Ariz.; Paul Gross, Stockton, Calif.; Rifat Pamukcu, Cincinnati, Ohio

[73] Assignees: Cell Pathways, Inc., Aurora, Colo.; University of Arizona, Tucson, Ariz.

[21] Appl. No.: 617,981

[22] Filed: Mar. 15, 1996

Related U.S. Application Data

[63] Continuation of Ser. No. 416,501, Apr. 4, 1995, abandoned, which is a continuation of Ser. No. 230,436, Apr. 19, 1994, abandoned, which is a continuation of Ser. No. 71,326, Jun. 2, 1993, abandoned, which is a continuation of Ser. No. 777,428, Oct. 11, 1991, abandoned, which is a continuation-in-part of Ser. No. 609,887, Nov. 6, 1990, abandoned.

[51] Int. Cl.$^6$ .............................. C08B 37/08; C07G 3/00; C07H 17/00; C07K 1/00
[52] U.S. Cl. .............................. 536/20; 536/4.1; 530/350; 514/55
[58] Field of Search .............. 536/20, 4.1; 530/350; 514/55

[56] References Cited

U.S. PATENT DOCUMENTS

| | | | |
|---|---|---|---|
| 3,313,848 | 4/1967 | Scherrer et al. | 562/454 |
| 3,337,570 | 8/1967 | Sherlock et al. | 564/442 |
| 3,415,834 | 12/1968 | Hoffmann et al. | 546/310 |
| 3,558,690 | 1/1971 | Sallmann et al. | 560/47 |
| 3,689,653 | 9/1972 | Sherlock et al. | 514/352 |
| 3,692,818 | 9/1972 | Boltze et al. | 560/47 |
| 3,714,226 | 1/1973 | Ruyle et al. | |
| 3,755,427 | 8/1973 | Adams et al. | 562/495 |
| 3,766,263 | 10/1973 | Godfrey | 562/465 |
| 3,839,344 | 10/1974 | Sherlock | 546/318 |
| 3,845,215 | 10/1974 | Godfrey | 514/557 |
| 4,045,576 | 8/1977 | Welstead, Jr. et al. | 562/436 |

FOREIGN PATENT DOCUMENTS 0 331 471  6/1989  European Pat. Off. ....... A61K 47/48

OTHER PUBLICATIONS

Stedman's Medical Dictionary, 24th Edition, p. 1120.
Harrison's Principles of Internal Medicine, Seventh Edition, pp. 1492–1493.
*Interaction of Indomethacin With Low Molecular Weight Chitosan, and Improvements of Some Pharmaceutical Properties of Indomethacin By Low Molecular Weight Chitosans*, International J. Pharm., vol. 67, pp. 11–20 (1991).
The Merck Index Therapeutic Category and Biological Activity Index, pp. 15–16 Merck Index (1989).
Martindale, The Extra Pharmacopoeia, The Pharmaceutical Press, London (1989).

*Primary Examiner*—John Kight
*Assistant Examiner*—Everett White
*Attorney, Agent, or Firm*—Brinks Hofer Gilson & Lione

[57] ABSTRACT

Esters and amides of substituted phenyl and pyridyl amino carboxylates are useful in the treatment of colonic polyps.

11 Claims, No Drawings

ESTERS AND AMIDES OF SUBSTITUTED PHENYL AND PYRIDYL AMINO CARBOXYLATES

RELATED APPLICATIONS

This application is a continuation of application Ser. No. (1) 08/416,501 filed on Apr. 4, 1995 (now abandoned), which is a continuation of Ser. No. (2) 08/230,436 filed on Apr. 19, 1994 (now abandoned), which is a continuation of Ser. No. (3) 08/071,326 filed on Jun. 2, 1993 (now abandoned), which is a continuation of Ser. No. (4) 07/777, 428 filed on Oct. 11, 1991 (now abandoned), which is a CIP of parent application (5) Ser. No. 07/609,887 filed Nov. 6, 1990 (now abandoned).

TECHNICAL FIELD

This invention relates to compositions and methods for treatment or prevention of colonic polyps.

BACKGROUND OF THE INVENTION

Each year in the United States alone, approximately 60,000 people die from colon cancer, and over 150,000 new cases of colon cancer are diagnosed. For the American population as a whole, individuals have a six percent lifetime risk of developing colon cancer, making it the second most prevalent form of cancer in the country. Colon cancer is also prevalent in Western Europe.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure, because most victims do not experience symptoms until the disease is advanced.

The incidence of colon cancer increases with age, particularly after the age of 40. Since the mean ages of populations in America and Western Europe are increasing, the prevalence of colorectal cancer should increase in the future.

In view of these grim statistics, efforts in recent years have concentrated on colon cancer prevention. Colon cancer usually arises from pre-existing benign growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy, procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common Sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps— literally covering the colon in some cases, making safe removal of the polyps impossible short of surgical removal of the colon. Because each polyp carries with it the palpable risk of cancerous development, polyposis syndrome patients invariably develop cancer if left untreated. Many of these patients have undergone a severe change in lifestyle as a result of surgery. Patients have strict dietary restrictions, and many must wear ostomy appliances to collect their intestinal wastes.

Recently, several non-steroidal anti-inflammatory drugs ("NSAIDs"), originally developed to treat arthritis, have shown effectiveness in inhibiting and eliminating polyps. Polyps virtually disappear when the patient take the drug. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in syndrome polyposis patients.

SUMMARY OF THE INVENTION

This invention is a novel class of compounds of formula I below that are effective in eliminating and inhibiting polyps, but are not characterized by the severe side reactions of NSAIDs.

This invention also relates to a method of treating patients with common sporadic polyps and polyposis syndromes to reduce or eliminate their polyps by administering to a patient in need of such treatment a physiologically effective amount of a compound of formula I.

DETAILED DESCRIPTION OF THE INVENTION

As discussed above, the present invention is a class of compounds of formula I

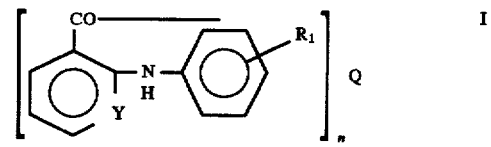

where Y is CH or N;

R$_1$ represents one or more substituents that are each attached to the aromatic ring independently selected from the group consisting of lower alkyl, lower haloalkyl, halo, alkoxy or benzyloxy;

Q is the deprotonated residue of a polymeric or macromolecular structure having a molecular weight of at least 1000 containing at least two primary and/or secondary amino groups and/or hydroxy groups; and n is an integer of at least 2.

As used herein, the term "halo" or "halogen" refers to chloro, bromo, fluoro and iodo groups, and the term "alkyl"

or alkoxy" refers to straight, branched chain or cyclic alkyl groups. The term "haloalkyl" refers to alkyl groups substituted with one or more halogens. The term "lower alkyl" refers to $C_1$–$C_6$ alkyl groups.

As used herein, the term macromolecule, macromolecular structure, or polymer refers to molecules having at least two primary and/or secondary amino groups, and/or hydroxy groups. Examples of such amino-containing polymers or macromolecules are polyvinylamine, polyallylamine, polyethyleneimine, chitosan, polyamino acids, polyamine exchange resins (e.g. Amberlite), polyaminoalkanes, and the like. Examples of hydroxy-containing polymers or macromolecules are polyhydroxyalkanes, polyvinylalcohols, carbohydrates (e.g. sucrose), polyethylene glycols, and the like. The term "deprotonated residue" includes the situation where at least some, but not all, of the amino and/or hydroxy groups are deprotonated on the macromolecule or polymer.

Compounds of this invention have unexpected utility for suppression of colonic polyps in view of the startling discovery that the effects of conventional NSAID therapy on colonic polyps can be, in fact, achieved via topical exposure to the agents. This effect was discovered in a patient with familial polyposis, a disease characterized by the presence of numerous colonic polyps. In an attempt to avoid colon cancer, the patient underwent surgical excision of the colon with formation of a continent ileostomy, or Kock's pouch. By this rarely performed surgical procedure, a pouch is constructed from the terminal portion of the small intestine. A colonic bacterial environment developed within the pouch resulting in extensive adenomatous polyp formation. Polyps also developed on the stoma, an external outlet from the pouch constructed from a contiguous portion of small intestine, and in the duodenum, the beginning of the small intestine. An NSAID, when administered in oral doses, led to the disappearance of the numerous polyps located in the pouch but not the polyps on the stoma or in the duodenum. Given the understanding of the metabolic and excretory patterns of the drug as well as of bacterial enzyme activation of the agent, these rare findings suggested that high local concentrations of the drug were responsible for the effects in the pouch. It was apparent from the lack of response of the polyps in the other locations, particularly the stomal polyps which are close to the pouch, that the effect was topical and that blood-borne or systemic delivery of the drug was ineffectual.

The topical effect is particularly surprising since the cells believed to be responsible for polyp growth and subsequent malignancy are not only epithelial cells deep within the crypts of the intestine, but may also include cells which modulate the local immunological defense mechanisms in deeper mucosal and serosal layers of the intestinal wall.

Compounds of this invention deliver active agents to the colon via the large macromolecular structure to which the active agent is conjugated. Colonic bacterial enzymes (or other colonic enzymes) cleave the active agent from the macromolecule, achieving locally high concentrations of the active agent and allowing the agent to contact the colon itself leading to inhibition of polyp proliferation.

The advantage of this treatment is that the active agent can be concentrated where it is effective, but whatever systemic levels are achieved are minimized. The systemic levels are particularly low because only passive absorption in the colon is involved. The negligible systemic levels are important in that the maintenance of chronic systemic levels of NSAIDs is complicated by a high incidence of gastric ulcers rendering them useless in a long-term prophylactic regimen.

Thus, contrary to prior approaches that relied on the high systemic levels of active agent to achieve the desired effect within the colon with the consequent gastric complications, the compounds of the present invention afford a different and safer therapeutic approach in light of the topical effect of these active agents on the colon itself.

The present invention also includes a method of treating patients with colonic polyps to reduce the polyps which comprises administering to the patient a therapeutically effective amount of a compound of formula I where Y, $R_1$ and n are as defined above, and Q is the deprotonated residue of a polyamine or polyhydroxy compound.

Compounds of Formula I may be formulated into compositions together with pharmaceutically acceptable carriers for parenteral injection, for oral administration in solid or liquid form, for rectal administration, and the like, although oral administration is most preferred.

Compositions according to the present invention for parenteral injection may comprise pharmaceutically acceptable sterile aqueous or nonaqueous solutions, suspensions or emulsions. Examples of suitable nonaqueous carriers, diluents, solvents or vehicles include propylene glycol, vegetable oils, such as olive oil, and injectable organic esters such as ethyl oleate. Such compositions may also contain adjuvants such as preserving, wetting, emulsifying and dispersing agents. They may be sterilized, for example, by filtration through a bacteria-retaining filter, or by incorporating sterilizing agents into the compositions. They can also be manufactured in the form of sterile soled compositions which can be dissolved in sterile water, or some other sterile injectable medium immediately before use.

Solid dosage forms for oral administration include capsules, tablets, pills, powders, troches and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets, troches and pills, the dosage forms may also comprise buffering agents. Tablets, pills and granules can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve polyp-eliminating activity in accordance with the desired method of administration. The selected dosage level therefore depends upon the nature of the active compound administered, the route of administration, the desired duration of treatment, and other factors. If desired, the daily dose may be divided into multiple doses for administration, e.g. two to four times per day.

Compounds of this invention can be made by one of the five general schemes below.

SCHEME I

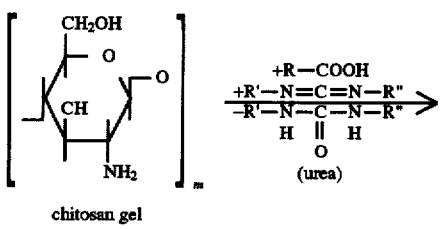

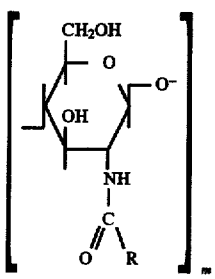

This scheme is useful for cases, where Q is water swellable polymer carrying aminogroups. The water soluble carbodiimide allows acylation in the alcoholic-aqueous phase, and the water soluble by-product urea can be removed by water, from the acylated polymer. The scheme allows acylation with carboxylic acid sensitive to the conditions of acid chloride or acid anhydride formation.

A chitosan gel $(GlcN)_m$ is prepared from chitosan, according to the method of S. Hirano et al. (Carbohyd. Res. 201 (1990) pp. 145–149) where m is the number of repeating units within the chitosan molecule. The gel is stirred in 70% aqueous methanol solution, at 0°–5° C., with the R-carboxylic acid (2 equivalents per GlcN; where R is the group in the brackets in formula I minus the attached carbonyl), and with a water-soluble carbodiimide (R'—N=C=N—R"; 2 equivalents per GlcN) for three days. (R' and R" are cycloalkyl or alkyl, and the like, containing also quaternary ammonium or sulfonate salt for solubilization of the carbodiimide). The resulting gel is homogenized, washed well with distilled water, stirred with NaOH (1.2 equivalents per GlcN) in water (50 ml per g of chitosan) for five days. The mixture is homogenized and washed to neutrality. The gel is then dried to an amorphous powder.

SCHEME II

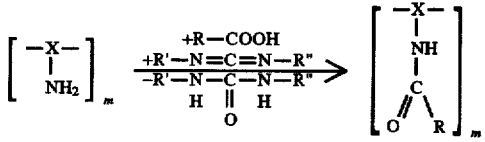

This scheme is useful for cases, where a salt between R—COOH and a polyamine Q is swellable or soluble in DMF. The carbodiimide is chosen, so that the by-product urea is soluble in dichloromethane, and therefore removable by extraction with it. Sodium hydroxide is used to extract unreacted R—COOH, so this scheme is useful for cases where acylation is difficult and incomplete. The scheme especially allows acylation with carboxylic acids that degrade under the conditions of acid chloride or acid anhydride formation.

$(GlcN)_m$ "chitosan," polylysine or similar polyamine "X" (0.01 mol-$NH_2$ groups; where m is the number of repeating amino-containing units per molecule of polyamine) are rapidly stirred in dimethylformanide ("DMF," 30 ml) at 50° C. until no further dissolution is apparent. The cooled (0°) mixture is treated with carbodiimide (R'—N=C=N—R"; 0.011 mol) with continued stirring for two days. The resultant solution or suspension is poured into ice water. The precipitate is filtered off and washed with water. It is purified by being homogenized with and filtered from (a) $CH_2Cl_2$ (2×50 ml); (b) 0.1N-NaOH (2×50 ml); (c) 0.1N-HCl (2×50 ml); (d) $H_2O$ (2×50 ml); and (e) ether (2×50 ml). The resultant powder Is dried.

SCHEME III

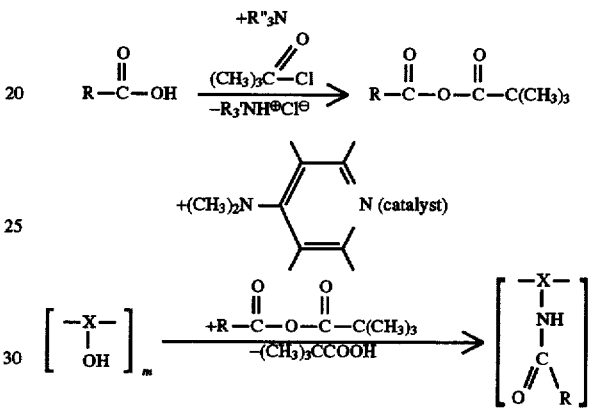

This scheme is suitable for cases were Q is a hydroxyl group-containing polymer that is soluble or swellable in dimethyl formamide. The bulky t-butyl group in pivalic acid prevents acylation by it, and dimethylamino pyridine catalyzes the difficult O-acylation. By-product pivalic acid is removable from the acylated polymer by extraction with organic solvent (e.g. toluene). The scheme is useful for carboxylic acids that are sensitive to the conditions of acylchloride synthesis.

Dry polyvinyl alcohol, methyl cellulose, or a similar swellable carbohydrate ($[X—OH]_m$; 0.01 mol-OH; where "m" is the number of repeating hydroxy-containing units in the polymeric compound) is rapidly stirred in absolute dimethyl formamide ("DMF," 50 ml) at 50° C. until no further dissolution is apparent. Separately the carboxylic acid (RCOOH; 0.01 mol) is dissolved in absolute tetrahydrofuran (30 ml). At −10° C., pivaloyl chloride (0.01 mol) is added, followed by drop wise addition of a tertiary amine ($R'_3N$) (0.01 mol, e.g., triethylamine, ethyl diisopropylamine). The precipitated amine hydrochloride is filtered off. The solution is added, drop by drop, to the stirred and cooled (−10° C.) polyol or carbohydrate mixture. The combined mixture is treated at −10° C. with p-dimethyl amino pyridine (0.0001 mol.), and is allowed to come to room temperature and stay there for 15 hours. Toluene (100 ml) is added, with stirring. The mixture is evaporated to dryness in a rotary evaporator. The residue is homogenized in and filtered from (a) toluene (100 ml) and (b) water (2×100 ml). The filtercake is dried in vacuo at 40° C. to constant weight.

SCHEME IV

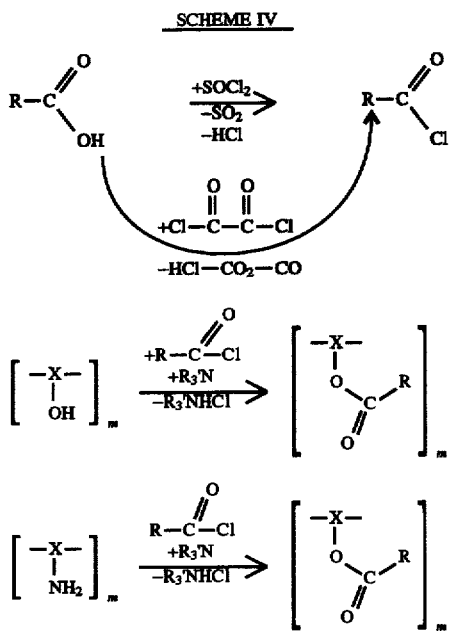

This scheme is useful for cases where Q is a polymer swellable in dimethyl formamide DMF), and where it needs a highly reactive reagent for acylation. The scheme is suitable for carboxylic acids that form stable acid chlorides.

Caroxylic acid (R—COOH; 0.01 mol) is refluxed with thionylchloride or oxalylchloride (20 ml) until solution is complete and gas evolution ceases. Excess reagent is removed by evaporation. The residual acid chloride is diluted with tetrahydrofuran (10 ml) to give solution A.

A polyamine ([—X—$NH_2$]$_m$) such as chitosan, aminoethyl cellulose, polylsine (0.01 mol-$NH_2$), or a polyhydroxy compound ([—X—OH]$_m$) such as polyvinyl alcohol or a carbohydrate (e.g. methyl cellulose; 0.01 mol-OH) are heated in absolute dimethyl formamide at 50° C., until no further dissolution is apparent. Pyridine (0.01 mol) and p-dimethylaminopyridine (0.01 mol) are added. The mixture is cooled to −10° C., and solution A is added slowly with stirring. After 15 hours at room temperature, toluene (100 mol) is added, and the solution is evaporated in vacuo. The residue is homogenized with and filtered from (a) water (2×100 ml); (b) ether (2×100 ml), and is dried.

SCHEME V

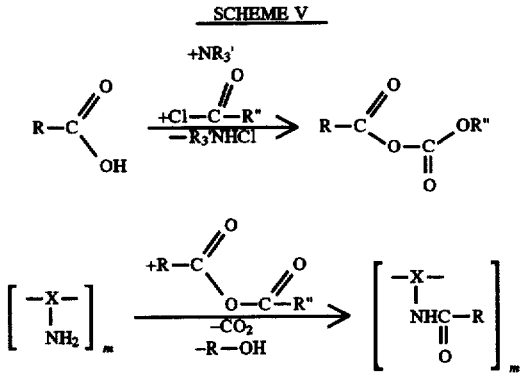

This scheme is useful, where Q is a polyamine swellable or soluble in dimethylformamide. It is especially suitable for cases where the removal of by-products such as salts, acids, or bases) from the final product is difficult, since in this case only carbon dioxide and low molecular weight alcohol are produced as by-products. The scheme is especially useful for carboxylic acids that decompose under the conditions of acid chloride synthesis.

Chitosan, amino ethyl cellulose, polylysine or a similar polyamine ([—X—$NH_2$]$_m$; 0.01 mol —$NH_2$ groups) is rapidly stirred in dimethyl formamide (30 ml) at 50° C. until no further dissolution is apparent.

The carboxylic acid (RCOOH; 0.01 mol) is dissolved in absolute tetrahydrofuran (30 ml). At first trialkylamine (NR'$_3$; 0.01 mol), and then alkylchlorocarbonate (Cl—COOR"; 0.01 mol, where R" is ethyl or isobutyl) is added. The precipitated trialkylammonium chloride (R'$_3$NHCl) is filtered off. The filtrate is added, with stirring, to the cold (−30° C.) polyamine solution. After being stored for 15 hours at −15° C., the mixture is poured on ice (300 g), with stirring. After the ice has melted, the precipitate is filtered off, is thoroughly washed with water, and is dried.

The foregoing may be better understood from the following examples, which are presented for purposes of illustration and are not intended to limit the scope of the invention. As used in the following examples, the references to compounds such as (1), (2), (3) etc., and to substituents such as R, $R_1$, $R_2$ etc., refer to the corresponding compounds and substituents in the foregoing reaction schemes and in formula L

EXAMPLE 1

Polyflufenamyl Chitosan

Flufenamic acid (0.02 mol.) is conjugated to chitosan gel (0.01 mol-$NH_2$) according to Scheme I. The procedure yields the desired compound ($R_1$=3-trifluoromethyl; Y=CH; Q=chitosan; m>50; n/m>0.2; n>10.)

EXAMPLE 2

Polymeclofenamyl Chitosan a) Mefenamic acid chloride

Mefenamic acid (o.726 g, 3 mmol) and 15 ml THF under argon were stirred at room temperature. Then 438 uL of thionyl chloride (0.714 g, 6 mmol, d=1.631) was added. This yellow mixture was stirred for 0.5 hour at room temperature, and then it was heated at 60–65 C. for 18 hours. The solvent was removed with rotary evaporation. Toluene (5–10 ml) was added, and it was again rotary evaporated. This was repeated two more times. Toluene was again added, and this yellow toluene solution was filtered and rotary evaporated to dryness giving a yellow solid (838 mg).

IR (HBr): 3360, 1700, 1620, 1565, 1500, 1460, 1420, 1320, 1250, 1200, 1120, 1040, 920, 865, 820, 775, 760, 740, 725, 660, and 490 cm$^{-1}$.

$^1$H NMR (CDCl$_3$): 2.18 ppm and 2.34 ppm (two triplets, 6H), 6.6 to 8.2 ppm consisted of a doublet at 6.6 ppm, a triplet at 6.7 ppm, a multplet at 7.1 and 7.3 ppm, and a doublet at 8.1 ppm, the total relative area of this region was 7; 9.85 ppm (s, 1H).

b) Polymeclofenamyl Chitosan

Meclofenamic acid cholride is conjugated to chitosan gel (0.01 mol-$NH_2$) according to Scheme I. The procedure yields the desired compound ($R_1$=2,6-dichloro,3-methyl;Q= chitosan Y=CH; m>50; n/m>0.2; n>10.)

EXAMPLE 3

Polyflunixyl Polylysine

Flunixin (0.01 mol.) is conjugated to polylysine (0.01 mol-$NH_2$) according to Scheme II. The procedure yields the desired compound ($R_1$=2-$CH_3$,3-trifluoromethyl; Y=N; Q=polylysine; m>50; n/m>0.2; n>10.)

EXAMPLE 4

Polymefenamyl Chitosan

Mefanamic acid (0.02 mol.) is conjugated to chitosan gel (0.01 mol-$NH_2$) according to Scheme I. The procedure yields the desired compound ($R_1$=2,3-dimethyl; Y=CH; Q=chitosan; m>50; n/m>0.2; n>10.)

EXAMPLE 5

Polyniflumyl Polylysine

Niflumic acid (0.01 mol.) is conjugated to polylysine (0.01 mol-$NH_2$) according to Scheme II. The procedure yields the desired compound ($R_1$=3-trifluoromethyl; Y=N; Q=polylysine; m>50; n/m>0.2; n>10.)

EXAMPLE 6

Polytolfenamyl Polylysine

Tolfenamic acid (0.01 mol.) is conjugated to polylysine (0.01 mol-$NH_2$) according to Scheme II. The procedure yields the desired compound ($R_1$=2-methyl,3-chloro; Y=CH; Q=polylysine; m>50; n/m>0.2; n>20.)

EXAMPLE 7

Polyflufenamic Ester Of Polyvinyl Alcohol a) Flufenamic acid chloride

Thionyl chloride (1.42 ml, 0.023 mol) was added to a suspended solution of 5 g (0.018 mol) of flufenamic acid in 30 ml toluene. The mixture was refluxed under nitrogen for 60 minutes. The solvent was removed in vacuo to give flufenamic acid chloride as a light red oil; IR(neat) 3354, 2954, 2923, 1749, 1712, 1667, 1576, 1519, 1377, 1311, 1193, 1121 $cm^{-1}$.

$^1$H NMR ($CDCl_3$): 6.8 to 8.4 PPM consisted of a triplet at 6.9 ppm, a doublet at 7.15 ppm, a multiplet at around 7.5 ppm, and a doublet at 8.25 ppm, the total relative area of this region was 8; 9.05 ppm (s, 1H).

b) Polyflufenamic ester of polyvinyl alcohol

Flufenamic acid chloride 5.32 g (0.017 mol) was added to 20 ml pyridine. To this solution mixture was added 1.57 g (0.031 mol) of polyvinyl alcohol ("PVA", average molecular weight of 50,000). The reaction mixture was slowly heated until all PVA dissolved and then refluxed for 60 minutes. The clear solution was concentrated in vacuo then washed with 100 ml of concentrated sodium bicarbonate solution. The aqueous part was decanted, and the residual oil was washed with five 200 ml portions of water to remove pyridine and unreacted PVA. The product was dried over phosphorus pentoxide ($P_2O_5$) in a vacuum desiccator at room temperature for 12 days. It gave 5.2 g of polyflufenamic ester of polyvinyl alcohol as a solid.

IR (film) 3336, 3326, 2941, 1735, 1678, 1657, 1601, 1583, 1521 $cm^{-1}$.

Elemental analysis calculated for $C_{18}H_{16}NO_3 \cdot \frac{1}{2}H_2O$, FW 360; % Theory: C, 60.00; H, 4.44; N, 4.00. % Found: C, 60.49; H, 4.67; N, 4.37.

The procedure yields the desired compound $R_1$=3-trifluoromethyl; Y=CH; Q=polyvinylalcohol; n/m=0.50.

EXAMPLE 8

Polyflufenamic Amide Of Polyethyleneimine

Flufenamic acid chloride (4.95 g; 0.017 mol) was prepared by the procedure of Example 7a and dissolved in 25 ml pyridine. To this solution was added 1.46 g (0.81 mmol) of polyethyleneimine (purity 99% and average molecular weight; 1800). The reaction mixture was stirred and refluxed for 60 min. The reaction mixture was concentrated in vacuo then washed with 100 ml of concentrated sodium bicarbonate solution. The aqueous part was decanted, and the residual oil was washed with five 200 ml portions of water to remove pyridine and unreacted polyethyleneimine. The product was dried over phosphorus pentoxide ($P_2O_5$) in a vacuum desiccator at room temperature for 12 days. It gave 3.1 g of polyflufenamic amide of polyethyleneimine as a solid.

IR (film) 3324, 2951, 2857, 1714, 1647, 1601, 1583, 1521, 1490, 1450, 1375, 1336, 1163 $cm^{-1}$.

Elemental analysis calculated for $C_{16}H_{13}N_2OF_3$; FW 306; % Theory: C, 62.74; H, 4.24. % Found: C, 63.15; H, 4.67.

The procedure yields the desired compound $R_1$=3-trifluoromethyl; Y=CH; Q=polyvinylalcohol; n/m=0.50.

EXAMPLE 9

Polymeclofenamyl Polyallylamine a) Meclofenamic acid chloride

Meclofenamic acid sodium salt (3.181 g, 10 mmol) and 50 ml toluene under argon were stirred at room temperature. Then 1.74 ml of oxalyl chloride (2.540 g, 20 mmol, d=1.455) was added. This yellow mixture was stirred for 30 minutes at room temperature, and then heated at 60°–65° C. for 18 hours. The solvent was removed with rotary evaporation. Toluene (5–10 ml) was added, and it was again rotary evaporated. This was repeated two more times. Toluene was again added, and the solution filtered and evaporated giving a yellow solid (2.931 g, 93%); mp 121.7–122.7; IR (KBr) 3340, 1690, 1610, 1570, 1455, 1415, 1310, 1240, 1200, 1175, 1125, 881, 810, 760, 741, 690, 670 $cm^{-1}$; $^1$H NMR ($CDCl_3$) 2.43 ppm (s, 3H, $CH_3$); 6.3–9 ppm (Ar H's, this region consisted of a doublet at 6.3 ppm, a triplet at 6.85 ppm, a multiplet at 7.25 to 7.4 ppm, a doublet at 9.25 ppm, and a singlet at 8.8 ppm the relative area was 6).

b) Polymeclofenamyl Polyallylamine

Polyallylamine hydrochloride (0.094, 1 mmol/allylamine unit) was dissolved in 250 µl of 1M KOH and stirred. Then 3 ml of tetrahydrofuran was added. Meclofenamic acid chloride (0.079 g, 0.25 mmol) was dissolved in 2 ml tetrahydrofuran and added to the polymer solution, and the polymer solution was stirred for 17 days at room temperature. The solvent was removed by rotary evaporation. Water (305 ml) was added, and it was again rotary evaporated. This was repeated two more times. The contents of the flask was then poured into a dialysis bag and dialyzed in a 50:50 mixture of methanol and water that was basified with sodium hydroxide. Dialysis was carried out for 13 days. The progress of dialysis was monitored by observing the UV absorption between 190–380 nm, the region where meclofenamic acid and its sodium salt strongly absorb. Then dialysis against water was carried out for 24 hours. The dialysis bag contents were concentrated by rotary evaporation and then lyophilized to yield 22 mg of the polymeclofenamyl polyallylamine as a fluffy off white solid.

IR (KBr): 3450, 3025, 1795, 1735, 1625, 1512, 1492, 1450, 1430, 1370, 1250, 1210, 1170, 1070, 870, 795, 740, 670 cm hu −1

Elemental analysis: % found C,46.45; H, 8.40; N, 14.60; Cl, 3.55.

The procedure yields the desired compound $R_1$=2,6-dichloro, 3-methyl; Q=polyallylamine; Y=CH; n/m=0.06.

EXAMPLE 10

Polyniflumic Ester of Polyvinyl Alcohol a) Niflumic acid chloride

Thionyl chloride (2.00 ml) was added to a suspended solution of 5 g (0.018 mol) of niflumic acid in 30 ml toluene. The mixture was refluxed under nitrogen for 45 minutes. The solvent was removed in vacuo to give niflumic acid chloride as a yellow oil. Purification by crystallization in a solvent mixture of toluene/petroleum ether gave 5.03 g of niflumic acid chloride as a solid. IR(NuJor Mull) 3380, 2948, 2912, 1710, 1615, 1600, 1460, 1402, 1377 cm$^{-1}$.

$^1$H NMR (CDCl$_3$): 6.8 to 8.6 ppm consisted of a quartet at 6.91 ppm, a doublet at 7.37 ppm, a triplet at 7.4 ppm, a doublet at 7.7 ppm, a singlet at 8.0 ppm, and a multiplet at around 8.5 ppm, the total relative area of this region was 7; 9.7 ppm (s, 1H).

b) Niflumic ester of polyvinyl alcohol

Niflumic acid chloride 5.03 g (0.017 mol) was dissolved in 150 ml of pyridine. To this solution was added 1.48 g (0.031 mol) of polyvinyl alcohol ("PVA", average molecular weight of 50,000). The reaction mixture was slowly heated until all PVA dissolved and then refluxed for 60 min. The clear solution was concentrated in vacuo then washed with 100 ml of concentrated sodium bicarbonate solution. The aqueous part was decanted and the residual oil was washed with five 200 ml portions of water to remove pyridine and unreacted PVA. The product was dried over phosphorus pentoxide (P$_2$O$_5$) in a vacuum desiccator at room temperature for 12 days. It gave 4.2 g of polyniflumic ester of polyvinyl alcohol as a solid.

IR (NuJor mull) 3336, 3061, 2927, 2889, 1723, 1667, 1607, 1584, 1491, 1377, 1132 cm$^{-1}$.

Elemental analysis calculated for C$_{17}$H$_{15}$N$_2$O$_3$F$_3$, FW 352; % Theory: C, 57.35; H, 4.26; N, 7.95. % Found: C, 57.26; H, 3.70; N, 8.47.

The procedure yields the desired compound R$_1$=3-trifluoromethyl; Y=N; Q=polyvinylalcohol; n/m=0.50.

It will be understood that various changes and modifications can be made in the details of procedure, formulation and use without departing from the spirit of the invention, especially as defined in the following claims.

We claim:

1. A compound of the formula:

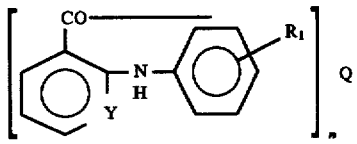

where Y is CH or N;

R$_1$ represents one or more substituents that are each attached to the aromatic ring independently selected from the group consisting of lower alkyl, lower haloalkyl, halo, alkoxy or benzyloxy;

Q is the deprotonated residue of a polymeric or macromolecular structure having a molecular weight of at least 1000 containing at least primary and/or secondary amino groups and/or hydroxy groups; and n is an integer of at least 2.

2. A compound according to claim 1 wherein Y is CH, and R$_1$ is selected from methyl, trifluoromethyl or chloro.

3. A compound according to claim 2 wherein R$_1$ is 2,3-dimethyl; 2-methyl,3-chloro; or 2,6-dichloro,3-methyl.

4. A compound according to claim 2 wherein R$_1$ is 3-trifluoromethyl; or 2-methyl, 3-trifluoromethyl.

5. A compound according to claim 1 wherein Y is N; and R$_1$ is selected from 3-trifluoromethyl; or 2-methyl,3-trifluoromethyl.

6. A method for treating patients having colonic polyps to reduce said polyps which comprises administering to said patient a therapeutically effective amount of a compound of the formula:

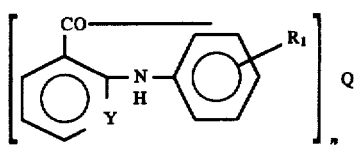

where Y is CH or N;

R$_1$ represents one or more substituents that are each attached to the aromatic ring independently selected from the group consisting of lower alkyl, lower haloalkyl, halo, alkoxy or benzyloxy;

Q is the deprotonated residue of a polyamine or polyhydroxy compound; and n is an integer of at least 2.

7. A method according to claim 6 wherein Y is CH, and R$_1$ is selected from methyl, trifluoromethyl or chloro.

8. A method according to claim 7 wherein R$_1$ is 2,3-dimethyl; 2-methyl,3-chloro; or 2,6-dichloro,3-methyl.

9. A method according to claim 7 wherein R$_1$ is 3-trifluoromethyl; or 2-methyl, 3-trifluoromethyl.

10. A method according to claim 6 wherein Y is N; and R$_1$ is selected from 3-trifluoromethyl; or 2-methyl,3-trifluoromethyl.

11. A method according to claim 6 wherein said compound is administered orally.

* * * * *